United States Patent [19]

Degen et al.

[11] Patent Number: 5,059,706

[45] Date of Patent: Oct. 22, 1991

[54] PROCESS FOR THE PREPARATION OF ALKYLHALOGENOSILANES

[75] Inventors: Bruno Degen, Much; Kurt Feldner, Leverkusen; Hans-Joachim Kaiser, Bergisch Gladbach; Manfred Schulze, Leichlingen, all of Fed. Rep. of Germany

[73] Assignee: Bayer Aktiengesellschaft, Leverkusen, Fed. Rep. of Germany

[21] Appl. No.: 497,466

[22] Filed: Mar. 21, 1990

[30] Foreign Application Priority Data

Apr. 3, 1989 [DE] Fed. Rep. of Germany ....... 3910665

[51] Int. Cl.$^5$ ............................................... C07F 7/16
[52] U.S. Cl. ................................................... 556/472
[58] Field of Search ........................................ 556/472

[56] References Cited

U.S. PATENT DOCUMENTS

| | | | |
|---|---|---|---|
| 4,602,101 | 7/1986 | Halm et al. | 556/472 |
| 4,898,960 | 2/1990 | Dosaj et al. | 556/472 |

FOREIGN PATENT DOCUMENTS

| | | |
|---|---|---|
| 0223447 | 5/1987 | European Pat. Off. . |
| 0272860 | 6/1988 | European Pat. Off. . |
| 0273635 | 7/1988 | European Pat. Off. . |

*Primary Examiner*—Paul F. Shaver
*Attorney, Agent, or Firm*—Sprung Horn Kramer & Woods

[57] ABSTRACT

A process for the preparation of alkylhalogenosilanes by reaction of silicon with an alkyl halide in the presence of a copper catalyst and promoter substances, the improvement wherein gaseous phosphorus compounds are admixed, as promotor substances, with the stream of alkyl halide.

3 Claims, No Drawings

PROCESS FOR THE PREPARATION OF ALKYLHALOGENOSILANES

The present invention relates to a process for the preparation of alkylhalogenosilanes by reaction of silicon with an alkyl halide in the presence of a copper catalyst and promotor substances. The present invention particularly relates to a process for the preparation of methylchlorosilanes, in which gaseous phosphorus compounds are admixed, as promotor substances, to the stream of methyl chloride.

The fundamental process for the preparation of methylchlorosilanes is direct reaction of ground silicon with methyl chloride in the presence of copper as a catalyst. The reaction is known to the expert as "Rochow synthesis" and is described in U.S. Pat. No. 2,380,995.

A mixture of methylchlorosilanes in which dimethyldichlorosilane is the main constituent is obtained by this process. In addition to methyltrichlorosilane, further methylchlorosilanes, such as e.g. trimethylchlorosilane, tetramethylsilane, methylhydridodichlorosilane and higher-boiling methylchlorodisilanes, are also formed.

Since the discovery of the synthesis, there has been a large number of activities concerned with improving the process for carrying out the synthesis and increasing the content of dimethyldichlorosilane, i.e. conducting the synthesis as selectively as possible in respect of the formation of dimethyldichlorosilane.

The latter is achieved above all by observing purity criteria with respect to the raw materials and by the controlled use of promotors. Some works have recently concentrated precisely on the use of promotors, of which the following may be mentioned below as example: DE-A 3 425 424, EP-A 138 678, EP-A 138 679, DE-A 3 501 085, EP-A 191 502, EP-A 194 214, EP-A 195 728 and EP-A 223 447.

The object of the present invention is likewise to conduct the process as selectively as possible in respect of dimethyldichlorosilane. The ratio of methyltrichlorosilane to dimethyldichlorosilane (T/D) is usually quoted in the literature as a measure for this. However, the aim of the present invention has moreover also been to reduce the content of trimethylmonochlorosilane, and in particular the content of high-boiling methylchlorodisilanes (70° C. < b.p. < 165° C.).

The present invention thus relates to a process for the preparation of alkylhalogenosilanes by reaction of silicon with an alkyl halide in the presence of catalysts and promotor substances, which is characterized in that the reaction is carried out in the presence of gaseous or readily volatile phosphorus compounds.

The use of phosphorus as a doping element of silicon/copper alloys is already described in DP 1 165 026. Nevertheless, the phosphorus was added to an Si/Cu alloy at above 1000° C., which is extremely energy-intensive. Ferrosilicon is moreover used as the source of silicon, a process which today by far no longer corresponds to the state of the art. Conclusively, it should be said that phosphorus must be added as a doping element to the solid ferrosilicon or the copper silicide phase before the reaction with methyl chloride.

A similar process is described in Russian Patent Application no. 754 859, and here also phosphorus is subjected to a sintering process together with copper and silicon.

EP-A 223 447 claims a process for the preparation of alkylhalogenosilanes from metallurgical silicon and alkyl halides in the presence of tin or tin compounds, copper or copper compounds in combination with a promotor, which must be elemental phosphorus, a metal phosphide or a compound which can form a metal phosphide under the conditions of direct synthesis.

Compounds which form metal phosphides under synthesis conditions, i.e. at 250°–350° C. in the presence of silicon, copper, tin and e.g. methyl chloride, are understood as being—according to the text of EP-A 223 447 on p. 13—alloys which contain phosphides which in turn are formed from the metals constituting the alloy during formation of the alloy; copper/phosphorus alloys containing 15 or 7% P are mentioned.

In all the cases described, phosphorus is employed in a form bonded as a solid or as the element.

EP-A 272 860 and EP-A 273 635 are to be understood in the same manner: In both cases phosphorus is employed as a trace element—contained in the silicon. Both cases are specific metallurgical doping methods in the preparation of silicon.

It was all the more surprising that gaseous or readily volatile phosphorus compounds, such as e.g. phosphorustrichloride, phosphorushydride, or even dimethylphosphite, have a positive influence on the course of the direct alkylhalogenosilane synthesis. Nowhere in the technical literature has such a reaction previously been described.

It is moreover a particular advantage over all the processes described previously, which require either a specific metallurgical pretreatment step or intimate mixing of solids in order to bring the small amounts of phosphorus, which are bonded as solids, into contact with the catalytically activated surface, if volatile phosphorus compounds which are easy to handle can be admixed to the gaseous stream of methyl chloride.

The volatile phosphorus compounds claimed here also do not have the predisposition of releasing metal phosphides, preformed in the solid, under the reaction conditions of direct synthesis of alkylhalogenosilanes, such as is described in EP-A 223 447 on p. 13. The present invention thus describes a reaction which is completely different from all the processes disclosed to date, in which phosphorus is active as a promotor in the direct synthesis of methylchlorosilanes.

In the preferred embodiment of the present invention, in the case of methylchlorosilane synthesis, not only an increased selectivity in respect of the ratio of methyltrichlorosilane to dimethyldichlorosilane, but also a reduction of the amount of trimethylmonochlorosilane obtained by about 50% and a reduced formation of higher-boiling methylchlorodisilanes of the boiling range 70° C. < b.p. < 165° C. is observed.

In the preferred embodiment of the present invention, the desired amount of the phosphorus compound is added, either discontinuously at short intervals or continuously, to the alkyl halide, which is passed continuously over the contact mass. The amount employed depends on the amount of contact mass employed in the experiment operated discontinuously (e.g. in the laboratory), and advantageously on the amount of fresh contact mass, which is usually likewise topped up continuously in the reactor, in the process conducted continuously. Optimum distribution of the similarly gaseous phosphorus compounds is ensured via the gas phase. The amount is between 20 and 2000 ppm, based on the fresh contact mass as described above; between 50 and 500 ppm are preferably employed. On the other hand, this is related to the phosphorus content of the particular phosphorus compound employed.

The use of volatile phosphorus compounds does not of course exclude the use of other promotor substances, such as e.g. zinc or zinc compounds, or similarly aluminum or aluminum compounds, and also tin and tin compounds.

The volatile phosphorus compound preferably employed is phosphorus trichloride. The use of the present invention is also not limited to a particular process technology in the direct synthesis, and the reaction can thus be conducted discontinuously or continuously, and it can be carried out either in a fluidized bed or stirred bed or in a fixed bed.

The following examples are intended to illustrate the present invention in more detail, but are in no way to be understood as limiting (% data denote wt. %).

EXAMPLE 1

All the following experiments were carried out in a stirred bed reactor of glass, internal diameter=30 mm, fitted with a spiral stirrer. The same amount of silicon of the same particle distribution of 71 to 160 μm was always employed in these experiments.

Methyl chloride was passed through the contact mass from the bottom via a glass frit under a pressure of 2 bar. The amount of methyl chloride was kept constant and was in all cases about 1.8 l/h under 2 bar. After the heating up and the start-up of the reaction, a stationary experimental phase was established at 300° C., and the amount of crude silane mixture formed per unit time was determined under the conditions thus specified. The values stated are always mean values of four individual determinations under framework conditions, kept constant, of: 2 bar, 1.8 l/h methyl chloride and 300° C.

The contact mass consisted of in each case 40 g silicon, 3.2 g copper catalyst and 0.05 g ZnO and was homogenized before use. The same catalyst was used in all cases.

| Experiment | Prod. Rate [g/h] | Mono [%]* | T/D | High-boiling constituents [%]** | |
|---|---|---|---|---|---|
| 1 | 5.1 | 2.2 | 0.050 | 6.4 | without vol. P comp. |
| 2 | 3.3 | 0.98 | 0.046 | 4.2 | 10 μl/h (MeO)$_3$P |
| 3 | 4.8 | 0.73 | 0.043 | 2.9 | 10 μl/h PCL$_3$ |
| 4 | 3.9 | 1.15 | 0.047 | 1.7 | 10 μl/h (MeO)$_2$P(O)H |
| 5 | 4.7 | 1.00 | 0.038 | 4.3 | 10 μl/h PH$_3$ |

Mono: trimethylmonochlorosilane
T/D: methyltrichlorosilane/dimethyldichlorosilane
*based on monomeric silane
**based on the total crude silane mixture

EXAMPLE 2

The experiments were carried out in the same apparatus under the same conditions described in example 1.

1.5wt. % ZnO and 0.1 wt. % (employed as SnO$_2$) were admixed as promotors to the copper catalyst.

| Experiment | Prod. Rate [g/h] | Mono [%]* | T/D | High-boiling constituents [%]** | |
|---|---|---|---|---|---|
| 6 | 6.2 | 2.53 | 0.059 | 4.1 | no vol. P comp. |
| 7 | 5.4 | 1.10 | 0.047 | 2.0 | 10 μl/h (MeO)$_3$P |
| 8 | 4.5 | 1.05 | 0.044 | 3.3 | 10 μl/h PCL$_3$ |
| 9 | 4.5 | 1.20 | 0.050 | 1.8 | 10 μl/h (MeO)$_2$P(O)H |
| 10 | 4.2 | 1.3 | 0.029 | 1.7 | 25 μl PCL$_3$ at the start of the reaction |

What is claimed is:

1. In a process for the preparation of alkylhalogenosilanes comprising by reacting silicon with an alkyl halide in the presence of catalysts and promoter substances, including phosphorus compounds the improvement comprising carrying out the reaction in the presence of gaseous or readily volatile phosphorus compounds.

2. A process according to claim 1, wherein the gaseous or readily volatile phosphorus compound is admixed with the alkyl halide before the reaction with the silicon.

3. A process according to claim 1, wherein the alkyl halide is methyl chloride.

* * * * *

UNITED STATES PATENT AND TRADEMARK OFFICE
CERTIFICATE OF CORRECTION

PATENT NO. : 5,059,706

DATED : October 22, 1991

INVENTOR(S) : Degen et al.

It is certified that error appears in the above-identified patent and that said Letters Patent is hereby corrected as shown below:

Col. 4, line 33    Delete " by reacting " and substitute -- reaction of --

Col. 4, line 35    After " compounds " insert -- , --

Signed and Sealed this

Ninth Day of November, 1993

Attest:

BRUCE LEHMAN

Attesting Officer

Commissioner of Patents and Trademarks